(12) United States Patent
Smith et al.

(10) Patent No.: US 7,457,660 B2
(45) Date of Patent: Nov. 25, 2008

(54) ELIMINATING INTERFACE ARTIFACT ERRORS IN BIOIMPEDANCE MEASUREMENTS

(75) Inventors: Kenneth Carless Smith, Toronto (CA); Joel Steven Ironstone, Toronto (CA)

(73) Assignee: Z-Tech (Canada) Inc., Toronto (CA)

( * ) Notice: Subject to any disclaimer, the term of this patent is extended or adjusted under 35 U.S.C. 154(b) by 575 days.

(21) Appl. No.: 10/722,511

(22) Filed: Nov. 28, 2003

(65) Prior Publication Data

US 2004/0181164 A1   Sep. 16, 2004

Related U.S. Application Data

(60) Provisional application No. 60/429,316, filed on Nov. 27, 2002.

(51) Int. Cl.
*A61B 5/00* (2006.01)
(52) U.S. Cl. .................................. 600/547; 600/300
(58) Field of Classification Search ................. 600/547, 600/587
See application file for complete search history.

(56) References Cited

U.S. PATENT DOCUMENTS

| | | | |
|---|---|---|---|
| 3,871,359 A | 3/1975 | Pacela | |
| 4,646,754 A * | 3/1987 | Seale | 600/587 |
| 5,197,479 A * | 3/1993 | Hubelbank et al. | 600/508 |
| 6,723,049 B2 * | 4/2004 | Skladnev et al. | 600/437 |
| 6,768,921 B2 * | 7/2004 | Organ et al. | 600/547 |
| 2001/0007056 A1 | 7/2001 | Linder et al. | |
| 2002/0079910 A1 | 6/2002 | Fukuda | |
| 2002/0123694 A1 | 9/2002 | Organ et al. | |

FOREIGN PATENT DOCUMENTS

WO       WO 96/32652       10/1996

OTHER PUBLICATIONS

Al-Hatib, Feras, Patient-instrument connection errors in bioelectrical impedance measurement, Physiological Measurement, IPO Publishing GB, vol. 19, No. 2, May 1998, pp. 285-296 XP002153191, ISSN: 0967-3334.
International Search Report.

* cited by examiner

*Primary Examiner*—Robert L Nassser
(74) *Attorney, Agent, or Firm*—Bereskin & Parr

(57) ABSTRACT

A system for diagnosing the possibility of disease in one of a first body part and a second substantially similar body part by impedance measurements is described. The system includes an impedance module for calculating impedances of corresponding segments of the first and second body parts from current and voltage signals. The measured impedances are corrected to account for the effect of stray impedances arising from non-body part sources.

30 Claims, 15 Drawing Sheets

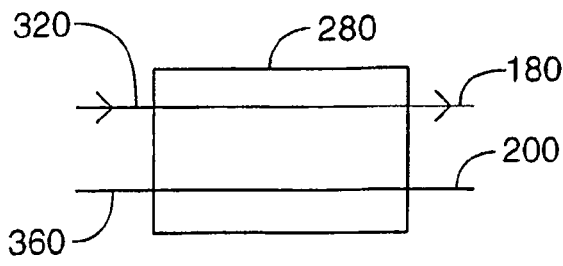
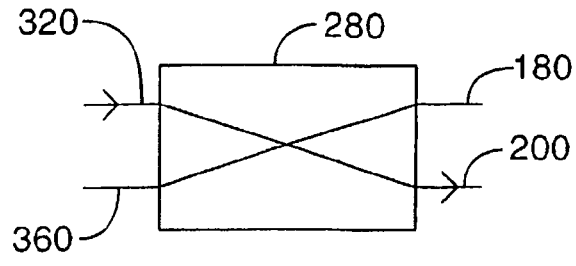
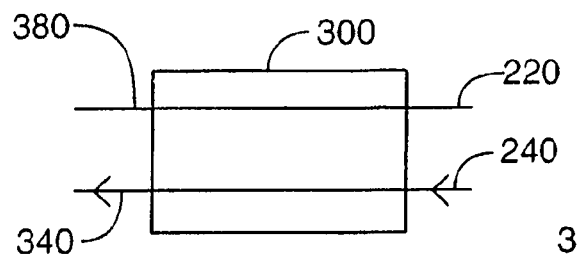
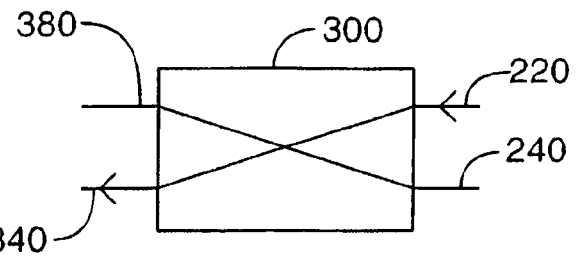
TETRAPOLAR
FIG. 9A     FIG. 9B
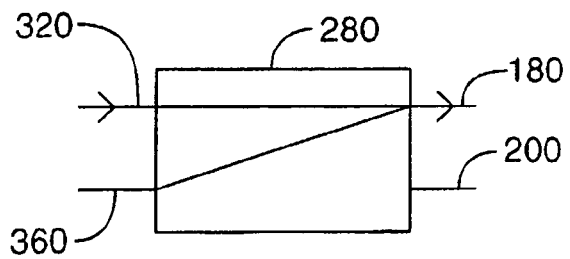
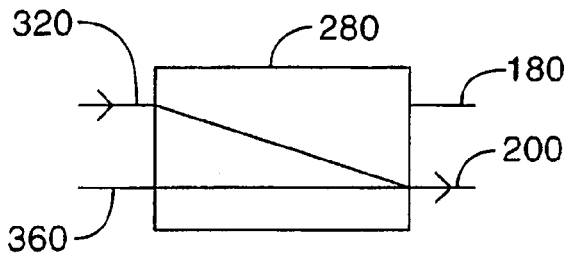
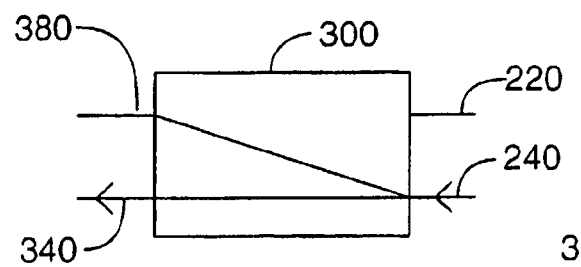
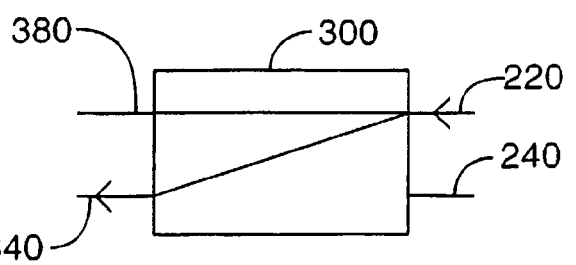
BIPOLAR
FIG. 9C     FIG. 9D

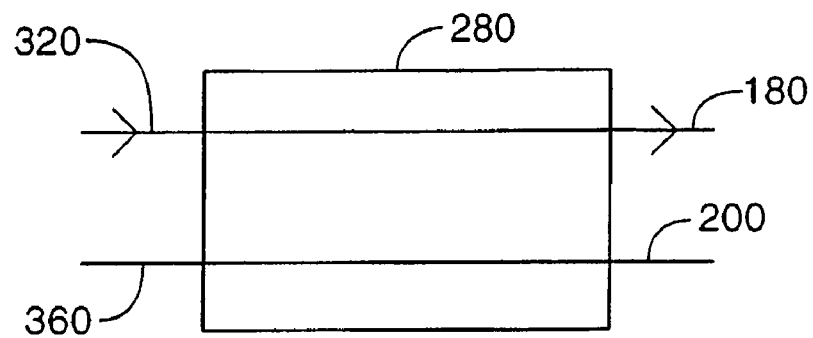
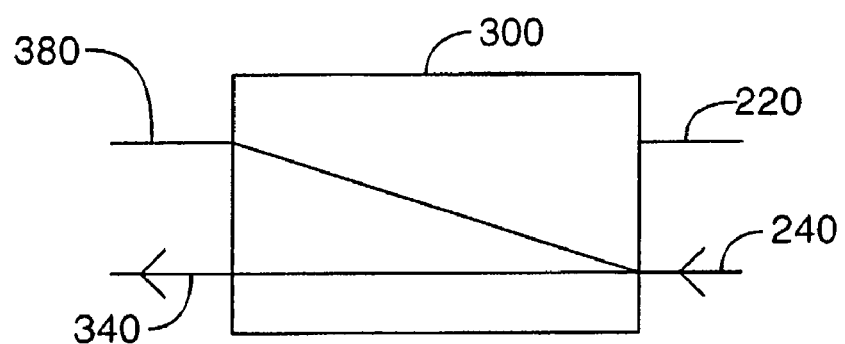
HYBRID
FIG. 10

ELIMINATING INTERFACE ARTIFACT ERRORS IN BIOIMPEDANCE MEASUREMENTS

CROSS-REFERENCE TO RELATED APPLICATION

This application claims the benefit of U.S. Provisional Application No. 60/429,316, filed Nov. 27, 2002, the entire contents of which is hereby incorporated by reference.

FIELD OF THE INVENTION

This invention relates to medical diagnosis of disease and specifically relates to diagnosis of disease using electrical impedances of body parts.

BACKGROUND OF THE INVENTION

The onset of disease is often accompanied by physical changes in a body part. Some physical changes, while not discernible by a patient, can be detected with appropriate diagnostic equipment, often at a relatively early stage of the disease. For example, the impedance of a body part in a patient can have diagnostic value.

Electrical impedances of various body tissues are well known through studies on intact humans or from excised tissue made available following therapeutic surgical procedures. In addition, it is well documented that a decrease in electrical impedance occurs in tissue as it undergoes cancerous changes. This finding is consistent over many animal species and tissue types, including, for example human breast cancers.

There have been a number of reports of attempts to detect breast tumors using electrical impedance imaging, such as, for example, U.S. Pat. No. 4,486,835. However, image fidelity and resolution can suffer when simplifying assumptions are made in mathematical models used to construct an image from impedance data.

Despite such difficulties, a method that permits comparisons of electrical properties for diagnostic purposes has been developed that involves homologous body parts, i.e., body parts that are substantially similar, such as a left breast and a right breast. In this method, the impedance of a body part of a patient is compared to the impedance of the homologous body part of the same patient. One technique for screening and diagnosing diseased states within the body using electrical impedance is disclosed in U.S. Pat. No. 6,122,544, which is incorporated herein by reference. In this patent, data are obtained from two anatomically homologous body regions, one of which may be affected by disease. Differences in the electrical properties of the two homologous body parts could signal disease.

Published international patent application, PCT/CA01/01788, which is incorporated herein by reference, discloses a breast electrode array for diagnosing the presence of a disease state in a living organism, wherein the electrode array comprises of a flexible body, a plurality of flexible arms extending from the body, and a plurality of electrodes provided by the plurality of flexible arms, wherein the electrodes are arranged on the arms to obtain impedance measurements between respective electrodes. In one embodiment, the plurality of flexible arms are spaced around the flexible body and are provided with electrode pairs, which can be used to make tetrapolar impedance measurements.

Tetrapolar impedance measurements are associated with injecting current between so called current electrodes and measuring a voltage drop between associated, but distinct, electrodes. In a preferred embodiment the differences between corresponding homologous impedance measurements in the two body parts are compared in a variety of ways that allows the calculation of metrics that can serve either as an indicator of the presence of disease or localize the disease to a specific breast quadrant or sector.

Despite the attractive features of this method of diagnosing disease in one of a homologous pair of body parts, there are some problems associated with this straightforward implementation. In particular, a number of factors may lead to systemic errors in the values of the measured tetrapolar impedance measurements. Because the diagnosis of disease hinges on detecting often small changes in the impedance of a body part, it is important that these systemic errors be eliminated or otherwise accounted for.

SUMMARY OF THE INVENTION

In circuits, the impedance Z is a complex number, whose real part is the resistance R and whose imaginary part is the capacitive reactance $X_c$. The magnitude of Z is given by $$|Z|=|V|/|I|,$$

and the phase of Z is given by $$\arg(Z)=\arg(V)-\arg(I),$$

where I denotes the current and V denotes the voltage. The system for diagnosing disease described herein measures impedance indirectly by first injecting a current of known amperage into a body part and then measuring the resultant voltage difference between electrodes. By using the preceding relations, the impedance can be obtained.

The impedances thus obtained are "raw" values that include spurious effects. Specifically, parasitic capacitance causes measured impedances to depend on the total interface impedance through which the current flows. This total interface impedance includes the skin of the patient, the conducting gel used to make contact between the skin and electrodes, and electrical components of the diagnostic system. The present invention provides a method for accounting for these non-body part sources of impedance.

In particular, a method and system for diagnosing the possibility of disease in one of a first body part and a second substantially similar body part by impedance measurements are described below. The system includes a first body part module for injecting a first current into the first body part and for receiving a corresponding first voltage signal, and a second body part module for injecting a second current into the second body part and for receiving a corresponding second voltage signal. The system further includes a correction module for obtaining a first correction factor for the first body part and a second correction factor for the second body part, the first and second correction factors accounting for impedance changes arising from non-body part sources. An impedance module calculates a first impedance from the first current, the first voltage signal and the first correction factor, and calculates a second impedance from the second current, the second voltage signal and the second correction factor. Several other similar measurements are performed to obtain a set of first impedances and a set of second impedances, which are used to diagnose the possibility of disease.

In one embodiment, the correction module includes a magnitude correction module for calculating a magnitude correction factor, and a phase correction module for calculating a phase correction factor, where the first correction factor is composed of the magnitude correction factor and the phase correction factor. The correction module includes a magnitude correction table to calculate the magnitude correction factor, the magnitude correction table containing calibration impedance magnitude ($|Z_{cal}|$) data and associated magnitude correction factor ($C_{mag}(|Z_{cal}|)$) data.

The system can further include a calibration apparatus to form the magnitude correction table, the calibration apparatus comprising an electrical model of the first body part, a variable interface resistance and the impedance module.

The impedance module can include a bipolar unit for calculating a bipolar impedance, $Z_{BP}$, from a bipolar voltage measurement made by the first body part module on the first body part, the magnitude of the bipolar impedance used by the correction module to obtain the correction factor. The correction module uses the magnitude correction table and the magnitude of the bipolar impedance to obtain the magnitude correction factor, which is given by $C_{mag}(|Z_{BP}|)$.

An uncorrected first impedance, $Z^{raw}$, is calculated by the impedance module from the first current and the first voltage signal. The magnitude of the first impedance, Z, is calculated by the impedance module according to $$|Z| = C_{mag}(|Z_{BP}|) \times |Z^{raw}|.$$

In one embodiment, the correction module includes a phase correction table, which is formed by a calibration apparatus, to calculate the phase correction factor, the phase correction table containing calibration impedance magnitude ($|Z_{cal}|$) data and associated phase correction factor ($C_{ph}(|Z_{cal}|)$) data. The calibration apparatus can include an electrical model of the first body part, a variable interface resistance and the impedance module.

The impedance module can include a bipolar unit for calculating a bipolar impedance, $Z_{BP}$, from a bipolar voltage measurement made by the first body part module on the first body part, the magnitude of the bipolar impedance used by the correction module to obtain the correction factor.

The correction module can use the information from the phase correction table and the magnitude of the bipolar impedance to obtain the phase correction factor $C_{ph}(|Z_{BP}|)$.

An uncorrected first impedance, $Z^{unc}$, is calculated by the impedance module from the first current and the first voltage signal. The phase of the first impedance, Z, is then calculated by the impedance module according to $$\arg(Z) = C_{arg}(Z_{BP}) \times \arg(Z^{unc}).$$

The present invention describes a system and/or method for measuring an electrical property, such as impedance, in a living tissue that includes a first body part module, a second body part module, a correction module and an impedance module, which are described below in more detail.

BRIEF DESCRIPTION OF THE DRAWINGS

FIGS. 9A-D shows modes of the controller switching unit of FIG. 8;

FIG. 10 shows a hybrid mode of the controller switching unit of FIG. 8;

DETAILED DESCRIPTION OF THE INVENTION

Figure 1:
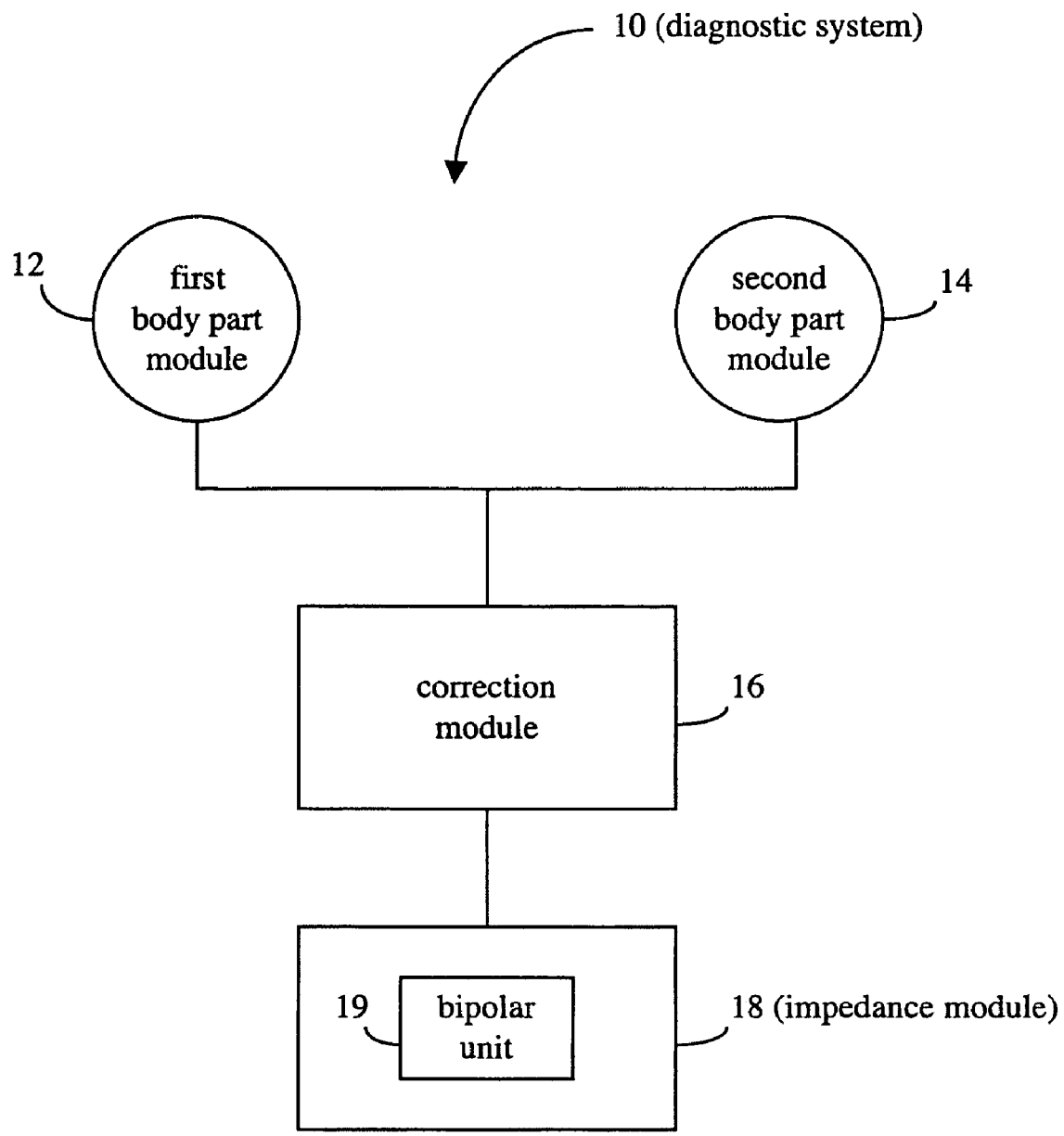
FIG. 1 shows a block diagram of the diagnostic system for diagnosing the possibility of disease according to the teachings of the present invention.

FIG. 1 shows a block diagram of the diagnostic system 10 for diagnosing the possibility of disease in one of a first body part and a second substantially similar body part by impedance measurements. The first body part and the second substantially similar body part are a homologous anatomical pair, such as a right breast (first body part) and a left breast (second body part).

The diagnostic system 10 includes a first body part module 12 and a second body part module 14. The system 10 also includes a correction module 16 and an impedance module 18, which includes a bipolar unit 19.

The first body part module 12 and the second body part module 14 are in contact with the skin that covers the respective body parts to obtain impedances thereof. The first body part module 12 injects a first current into the first body part and receives a corresponding first voltage signal. Similarly, the second body part module injects a second current into the second body part and receives a corresponding second voltage signal. In tetrapolar measurements, two electrodes are used to inject and receive current, and two different electrodes are used to measure the corresponding voltage difference therebetween. It should be understood that in some embodiments of the present invention, the first and second body part modules 12 and 14 might coincide. In such embodiments, a single body part module is used to first make measurements on the first body part. Subsequently, the same body part module is used to make measurements on the second body part.

The correction module 16 obtains a first correction factor for the first body part and a second correction factor for the second body part. As described in more detail below, these correction factors are used to account for stray impedances inherent in non-body part sources. For example, as the impedance of the skin changes, more or less current is driven through non-body part sources. Likewise, impedance that is inherent in the electronic components of the diagnostic system 10 can also yield spurious results if this impedance is not properly accounted for.

The impedance module 18 calculates a first impedance from the first current, the first voltage signal and the first correction factor, and similarly calculates a second impedance from the second current, the second voltage signal and the second correction factor. Assuming that at least one of the body parts is healthy, a significant difference between the impedances of the first and second body parts might indicate a presence of disease, while a similarity between the two might indicate an absence of disease. The impedance unit 18 also includes the bipolar unit 19 used to make bipolar impedance measurements during a calibration stage described in more detail below.

Figure 2:
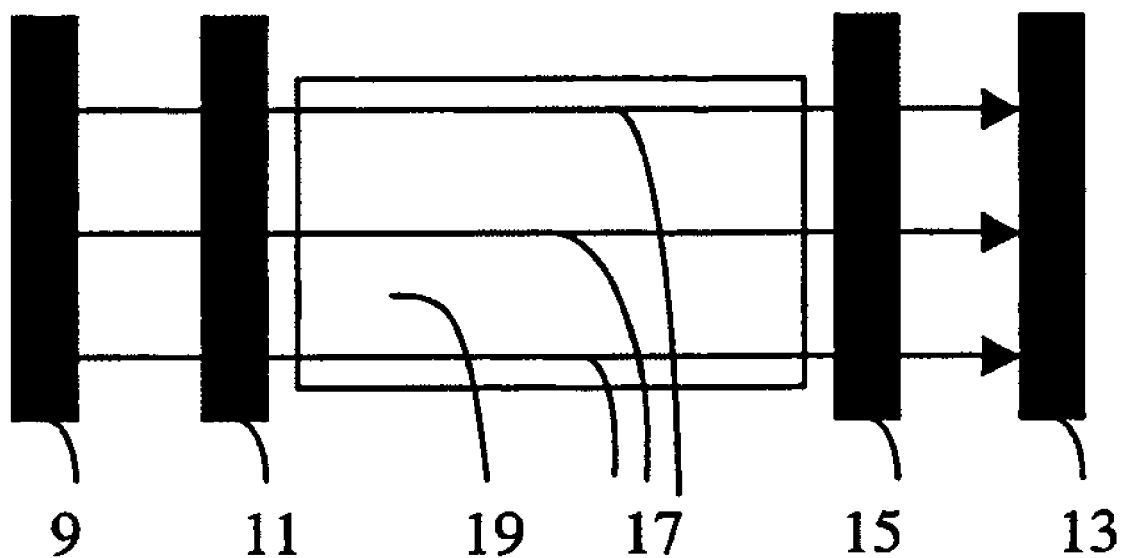
FIG. 2 shows four electrodes of the first body part module of FIG. 1.

FIG. 2 shows four electrodes 9, 11, 13 and 15 of the first body part module 12 of FIG. 1. The four electrodes 9, 11, 13 and 15 and the impedance module 18 are used to calculate an electrical impedance of the first body part of the patient by the tetrapolar method. It should be understood that in typical applications, the first body part module 12 includes more than the four electrodes 9, 11, 13 and 15 shown in FIG. 2.

The electrode 9 is a current injection electrode and the electrode 11 is a voltage measurement electrode. Electrodes 9 and 11 form one pair of associated electrodes. Likewise, the electrode 13 is another current injection electrode, and the electrode 15 is an associated voltage measurement electrode.

The arrows 17 indicate the current flowing between electrodes 9 and 13. The current injection electrodes 9 and 13 are used to inject current into the first body part, such as a right breast, and to remove current from the breast, respectively. The voltage measurement electrodes 11 and 15 are used to measure the voltage that is produced across the breast tissue 19, by the current. By using separate electrode pairs for current injection and voltage measurement, series impedance associated with measurement leads is ignored, and a more accurate measurement of impedance can be produced. However, stray impedances can produce artifacts in the experimental results that could affect the accuracy of the diagnosis of disease of the breast based on the tetrapolar impedance measurements. The correction module 16 can be used to account for these stray impedances.

Figure 3:
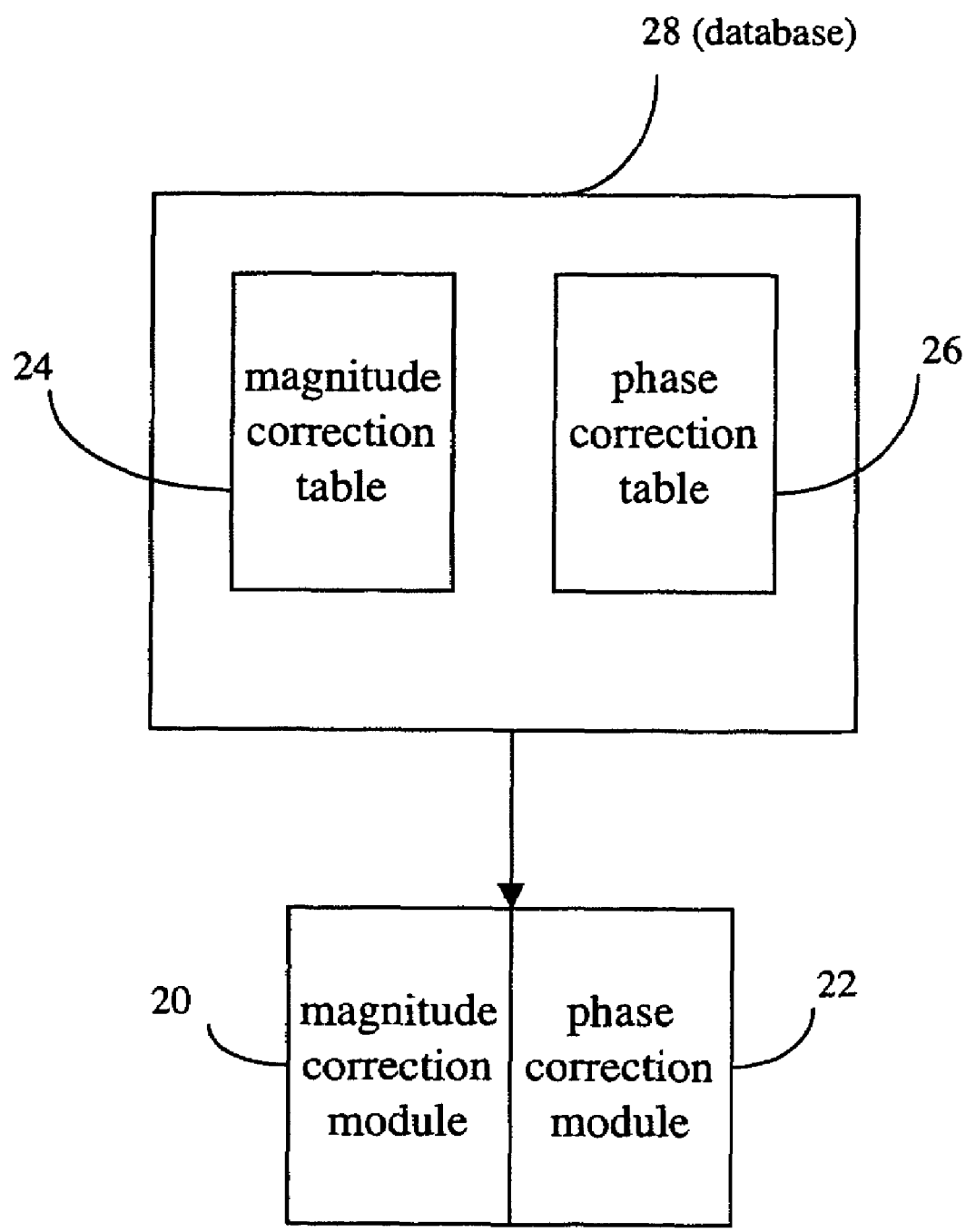
FIG. 3 shows a block diagram of the correction module of FIG. 1.

FIG. 3 shows a block diagram of the correction module 16 of FIG. 1. The correction module 16 includes a magnitude correction module 20, a phase correction module 22, a magnitude correction table 24, a phase correction table 26 and a database 28.

The first correction factor is composed of a magnitude correction factor, calculated by the magnitude correction module 20, and a phase correction factor, calculated by the phase correction module 22.

The magnitude correction table 24 contains calibration impedance magnitude ($|Z_{cal}|$) data and associated magnitude correction factor ($C_{mag}(|Z_{cal}|)$) data. The correction module 16 uses the magnitude correction table 24 to calculate the magnitude correction factor.

Likewise, the phase correction table 26 contains calibration impedance magnitude ($|Z_{cal}|$) data and associated phase correction factor ($C_{ph}(|Z_{cal}|)$) data. The correction module 16 uses the phase correction table 26 to calculate the phase correction factor. The magnitude correction table 24 and the phase correction table can be stored in the database 28 as separate tables, or can be amalgamated into one table.

In one embodiment, the magnitude correction table 24 includes a list of calibration impedance magnitudes, $|Z_{cal}|$, and associated magnitude correction factors $C_{mag}(|Z_{cal}|)$. Similarly, the phase correction table includes a list of calibration impedance magnitudes, $|Z_{cal}|$, and associated phase correction factors $C_{ph}(|Z_{cal}|)$. The correction module 16 interpolates values from the correction tables to obtain the appropriate magnitude and phase correction factors.

In another embodiment where the calibration impedance magnitudes and associated magnitude correction factors describe a curve, these data pairs can be captured with just a few parameters. For example, when the curve is a straight line, instead of storing several pairs of calibration impedance magnitudes, and their associated magnitude correction factor, it suffices to store just two numbers, a slope and intercept, which completely defines the line. Similarly, when the phase data describe a simple curve, a few parameters can be stored in the phase correction table to characterize the data. The slope and the intercept, instead of the actual tabular values, can be stored in the database 28 and used to interpolate to find appropriate correction factors, as described below.

The first body part module 12 and the second body part module 14 are placed on the respective body parts of the patient. The impedance module 18 generates currents and measures resulting voltages. These measurements yield raw impedance values of the patient. These raw values are subject to errors arising from stray impedances in the patient and in the measurement apparatus. The correction factor, which includes the magnitude correction factor and the phase correction factor, is used to correct the magnitude and the phase of the raw impedance, respectively, as is described in greater detail below. The corrected impedances may then be used to diagnose the possibility of disease.

Figure 4:
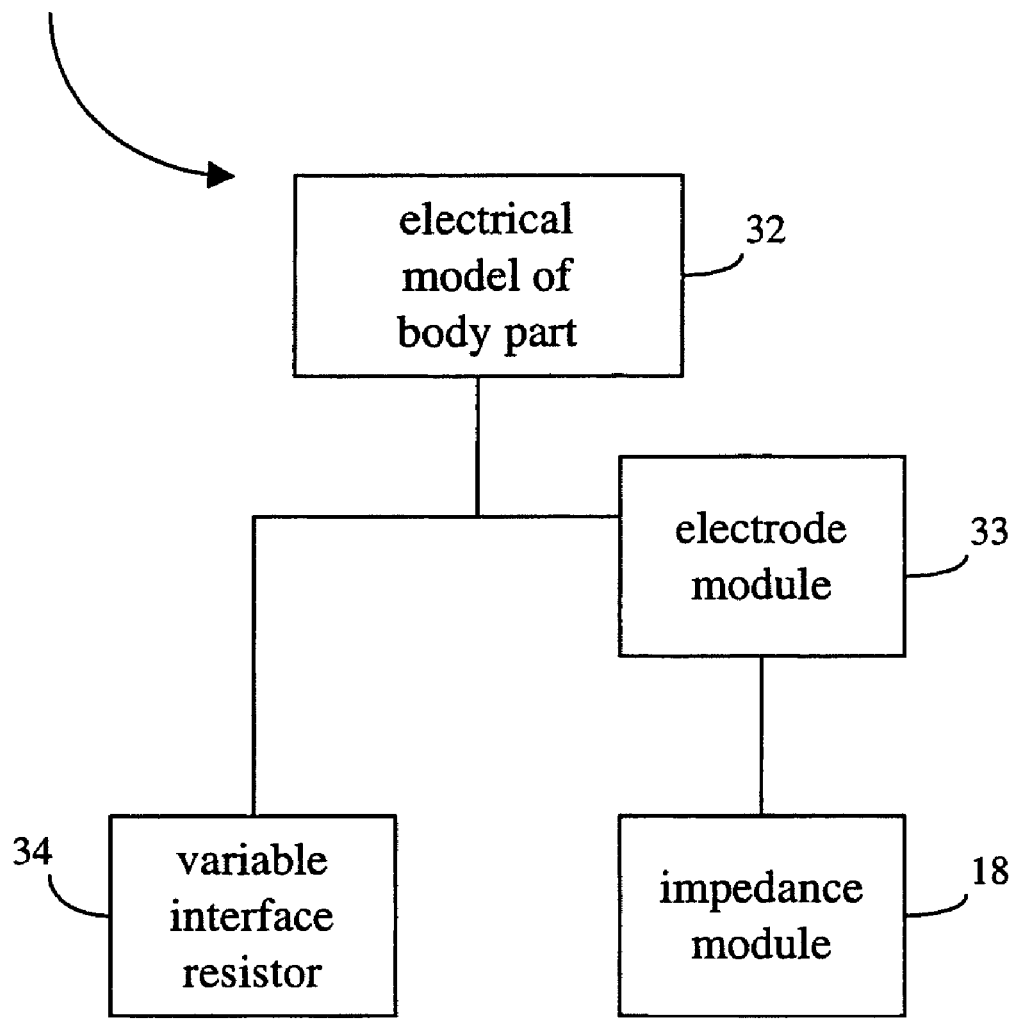
FIG. 4 shows a block diagram of the calibration apparatus used to obtain the magnitude correction table and the phase correction table of FIG. 3.

FIG. 4 shows a block diagram of a calibration apparatus 30 used to obtain the data in the magnitude correction table 24 and the phase correction table 26 of FIG. 3. The calibration apparatus 30 includes an electrical model 32 of the first (or second) body part, an electrode module 33, a variable interface resistor 34, and the same impedance module 18 used to make impedance measurements in the patient.

The calibration apparatus 30 is used during a calibration phase, in which the calibration apparatus 30 obtains the correction data of the tables 24 and 26. During the calibration phase, instead of connecting the impedance module 18 to a patient, the impedance module 18 is connected to the first body part electrical model 32. The first body part electrical model 32 is an electrical device that models the first body part.

The electrode module 33 includes a multiplexer similar to one present in the first body part module 12 or the second body part module 14. In addition, the electrode module 33 includes electrodes that correspond to the electrodes in the first body part module 12 that connect to the first body part of the patient. The variable interface resistor 34 models the resistance of electrical components of the first body part module 12, the patient's skin, and any gel used to establish a contact therebetween.

Figure 5:
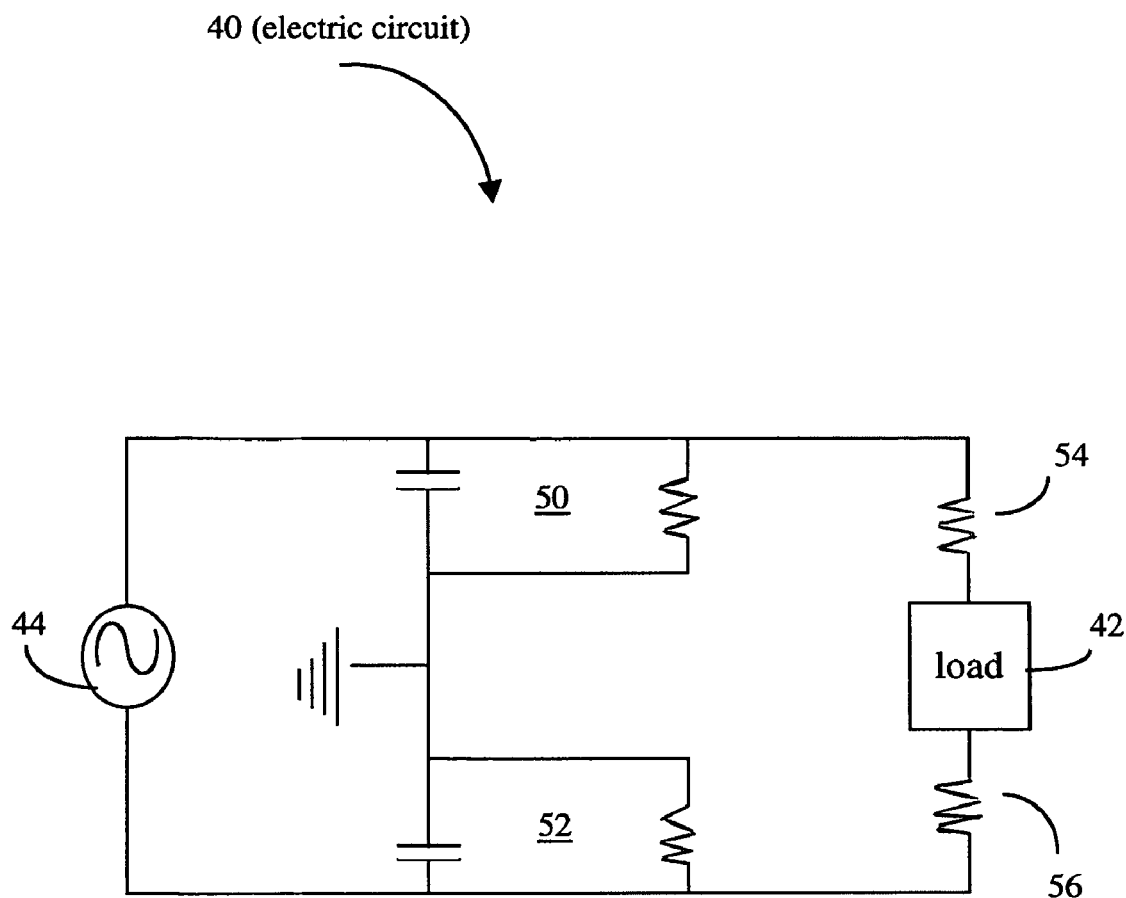
FIG. 5 is an electrical circuit that corresponds to the calibration apparatus of FIG. 3.

FIG. 5 is an electrical circuit 40 that corresponds to the calibration apparatus 30 of FIG. 4. The electrical circuit 40 includes a load 42 having a known resistance, $R_{load}$. The load 42 corresponds to the body part electrical model 32, which models the body part. The electric circuit 40 further includes a source 44 of balanced alternating current, two shunts 50 and 52, and two interface resistors 54 and 56.

The shunts 50 and 52 model crosstalk between cables connecting the various components of the diagnostic system 10, such as cables connecting the impedance module 18 to the first body part module 12 (or second body part module 14). The shunts 50 and 52 also account for shunt elements in switches present in a multiplexer of the body part module 12. The interface resistors 54 and 56, which correspond to the variable interface resistor 34 of FIG. 4, represent the resistance of the multiplexer in the first body part module 12 and the skin, and any gel used to establish a contact between the first body part module 12 and the skin.

The sum of the load resistance and the interface resistance is the magnitude of the calibration impedance:

$$|Z_{cal}| = R_{load} + R_{interface}$$

As $R_{interface}$ increases, more current is diverted through the shunts 50 and 52 and less flows through the load 42. The resultant voltage drop across the load 42 also decreases, resulting in a smaller calculated impedance magnitude. This drop in impedance has an analog in real measurements of patients. Increases in the resistance of the skin and instrument tend to decrease the measured impedance through the body part. Unless this effect is corrected, a faulty diagnosis might be made. The calibration apparatus 30 is used to correct this problem.

The ratio of the impedance calculated from voltage measurements across the electrical model of the body part 32, corresponding to the load 42, to the actual (or expected) impedance, $R_{load}$, is the magnitude correction factor, $C_{mag}$ at the calibration impedance magnitude of $|Z_{cal}|$. By varying $R_{interface}$, and then measuring the impedance across the electrical model of the body part, a plot can be obtained of $C_{mag}$ versus $|Z_{cal}|$.

Figure 6:
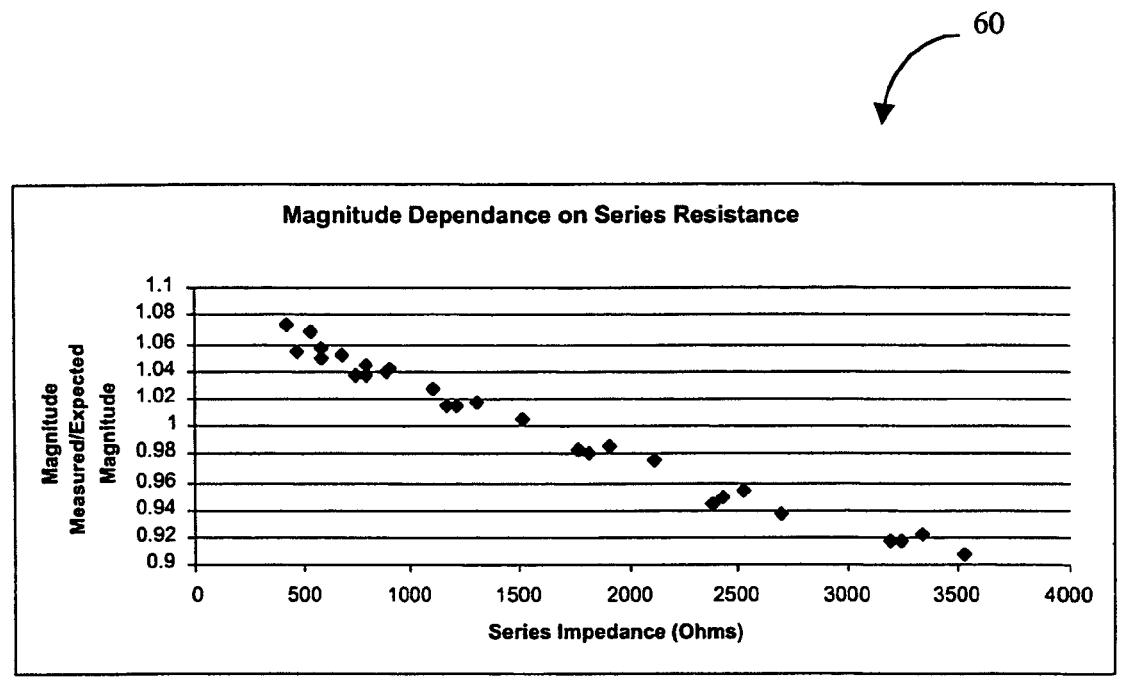
FIG. 6 shows a plot of magnitude correction factor as a function of calibration impedance magnitude, according to the teachings of the present invention.

FIG. 6 shows such a plot 60 of $C_{mag}$ versus $|Z_{cal}|$. As expected, $C_{mag}(|Z_{cal}|)$ is a decreasing function. The data points constituting the plot can form the magnitude correction table 24. The information in the magnitude correction table 24 can be used to find $C_{mag}$ at arbitrary values of $|Z_{cal}|$ by interpolation. Alternatively, a best-fit curve through the data of plot 60 can be found. For example, plot 60 approximately describes a straight line. The slope and intercept of the straight line can be used to interpolate data points to find appropriate correction factors.

Similarly, a phase calibration table can be constructed. For this purpose the calibration impedance magnitude, $|Z_{cal}|$, can be varied and the change in the phase of the impedance across the load 42 measured. The change in phase at a particular $|Z_{cal}|$ is $C_{phase}(|Z_{cal}|)$.

Figure 7:
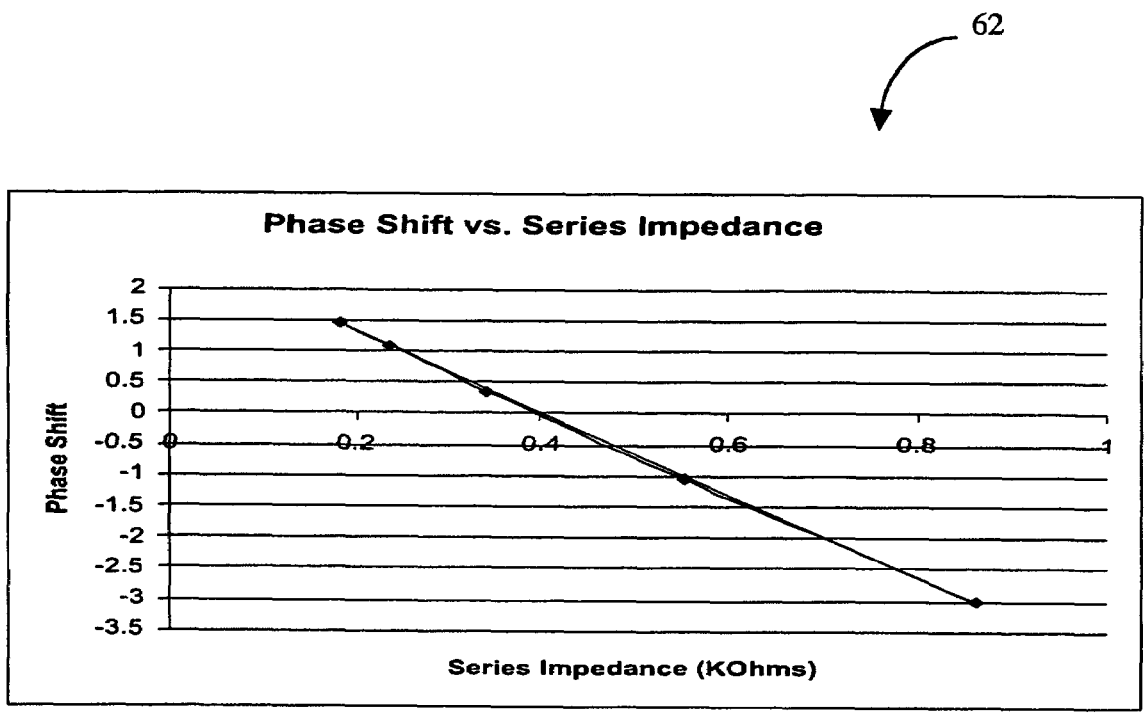
FIG. 7 shows a plot of phase correction factor as a function of calibration impedance magnitude, according to the teachings of the present invention.

FIG. 7 shows a plot 62 of $C_{phase}$ versus $|Z_{cal}|$. The data corresponding to this plot 62 can be stored in the memory of a computer (not illustrated) as the phase correction table 26.

The impedance module 18 uses these tables 24 and 26 to correct the raw impedances measured from a patient. In particular, if $Z^{raw}$ is the raw impedance, as calculated by the impedance module 18 from the currents injected into the patient and the resulting voltages, then the corrected values, Z, can be obtained using the correction factors.

To find the appropriate correction factor to use, a bipolar measurement is performed on the patient. In particular, a first electrode of the first body part module 12 is used to inject current while a second electrode withdraws current from the first body part. In a bipolar measurement, these same two electrodes are also used to measure the voltage difference therebetween. From the values of the current and voltages, the bipolar unit 19 of the impedance module 18 finds a bipolar impedance, $Z_{BP}$. The magnitude of this bipolar impedance is associated with the magnitude of the calibration impedance, $|Z_{cal}|$.

Thus, the diagnostic system 10 makes two measurements, obtaining the bipolar value $Z_{BP}$ and the tetrapolar value $Z^{raw}$. The correction factors $C_{mag}(|Z_{BP}|)$ and $C_{phase}(|Z_{BP}|)$ are used to correct the raw tetrapolar impedance according to:

$$|Z|=C_{mag}(|Z_{BP}|) \times |Z^{raw}|$$

$$\arg(Z)=\arg(Z^{raw})+C_{phase}(|Z_{BP}|)$$

The magnitude and phase of the corrected impedance may then be used for diagnosis of disease, as described, for example, in U.S. Pat. No. 6,122,544.

Because the diagnostic system 10 performs and utilizes both bipolar and tetrapolar measurements, a system is required that is capable of performing both. Such as system is now described.

Figure 8:
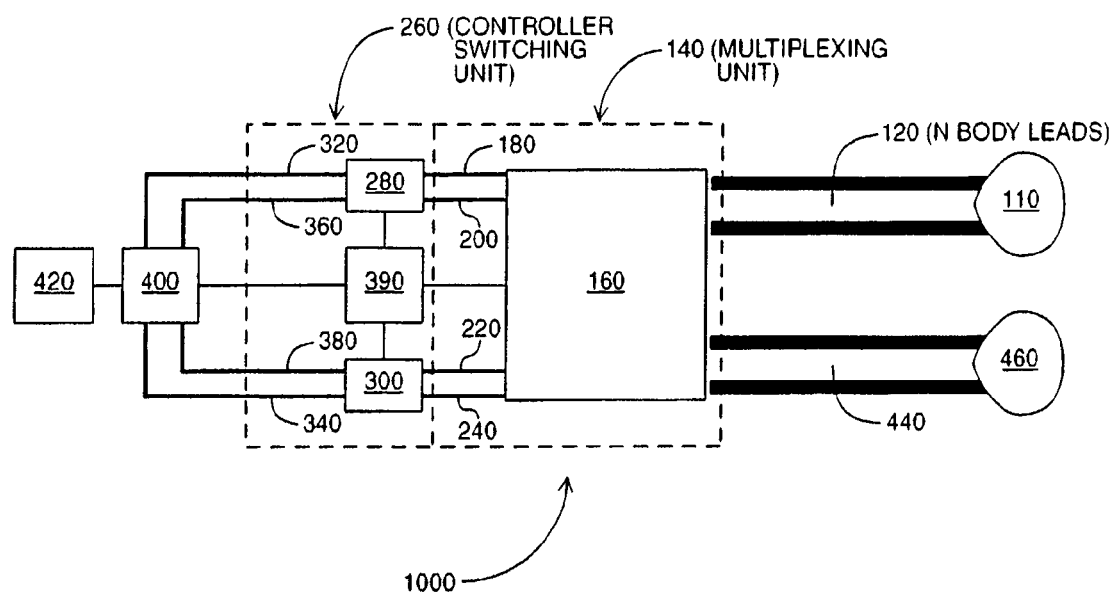
FIG. 8 shows a block diagram of a system for measuring a voltage in a body part, according to the teachings of the present invention.

FIG. 8 shows a system 1000 for measuring a voltage in a body part 110, such as a human breast. The system 1000 includes N body leads 120. In what follows, the N body leads 120 are ordered from 1 to N for reference. The system 1000 also includes a multiplexing unit 140 having a multiplexer 160, a first MX lead 180, a second MX lead 200, a third MX lead 220 and a fourth MX lead 240.

The system 1000 further includes a controller switching unit 260 having a first switch 280 connected to the multiplexer 160 by the first MX lead 180 and the second MX lead 200, a second switch 300 connected to the multiplexer 160 by the third MX lead 220 and the fourth MX lead 240, a current input lead 320 connected to the first switch 280, a current output lead 340 connected to the second switch 300, a first voltage lead 360 connected to the first switch 280, and a second voltage lead 380 connected to the second switch 300. The controller switching unit 260 also includes a controller 390. The system 1000 further includes an impedance module 400 and a diagnosis module 420.

Also shown in FIG. 8 is an optional second set of leads 440 that can be used when making measurements on a second homologous body part 460. The description below is directed mainly to an impedance measurement on the one body part 110 with the set of N leads 120, but it should be understood that the discussion could be analogously expanded to include an impedance measurement on the second homologous body part 460 with the second set of leads 440. Thus, the principles of the present invention can be applied to diagnosis of disease by making electrical measurements on a single body part, or by making measurements on a homologous pair of body parts. When making measurements on only a single body part, the results can be compared to standard results obtained from population studies, for example, to diagnose disease. When using a homologous pair of body parts, the results of one body part can be compared to the results of the homologous body part of the same patient, as described in U.S. Pat. No. 6,122,544.

The N body leads 120 electrically connect the multiplexing unit 140 to the body part 110. Each of the N body leads 120 includes a wire capable of carrying a current and an electrode to attach to the body part 110. A current conducting gel can act as an interface between the electrode and the skin covering the body part 110.

The multiplexing unit 140 and the controller switching unit 260 allow a current to flow through the body part 110 between any two body leads, $n_1$ and $n_2$, of the N body leads 120, and a resultant voltage to be measured between any two body leads, $n_3$ and $n_4$ of the N body leads 120, where $n_1 \neq n_2$ and $n_3 \neq n_4$, but where $n_1$, $n_2$, $n_3$ and $n_4$ need not otherwise be distinct. Thus, $n_1$, $n_2$, $n_3$, and $n_4$ are numbers belonging to the set $\{1, 2, \ldots, N\}$ that identify body leads. For example, if $n_1=7$, then $n_1$ denotes the seventh body lead from among the N body leads 120 used to inject current into the body part 110.

The impedance module 400 generates current that is injected into the current input lead 320 and then delivered to the body part. The current output lead 340 receives the current from the body part. When the current is traveling through the body part, the first voltage lead 360 and the second voltage lead 380 are used to measure the resultant voltage between these leads 360 and 380. The impedance module 400 uses this voltage, together with the known current injected into the current input lead 320, to calculate a corresponding impedance, which may then be used by the diagnosis module 420 to diagnose disease.

In one embodiment, N is even and the multiplexer 160 can electrically connect the first MX lead 180 and the fourth MX lead 240 to a first set of N/2 of the N leads, and the second MX lead 200 and the third MX lead 220 to a second set of the other N/2 leads. In a conventional system, the first set of N/2 leads are exclusively used to inject current into and receive current from the body part. The second set of N/2 leads are then exclusively used to measure resultant voltages in tetrapolar measurements. This configuration limits the number of impedances that can be measured.

In the system 1000, however, the second set of N/2 leads can also be used to inject and receive current, and the first set can be used to measure resultant voltages. Thus, the system 1000 can furnish a greater number of impedances. Moreover, as detailed below, the system can make both tetrapolar and bipolar measurements. The added benefits arise from the functionality of the controller switching unit 260. By using the controller switching unit 260, the system 1000 can force current to flow through the body part 110 between any two body leads, $n_1$ and $n_2$, of the N body leads 120, and a resultant voltage to be measured between any two body leads, $n_3$ and $n_4$ of the N body leads 120, where $n_1 \neq n_2$ and $n_3 \neq n_4$.

FIGS. 9A-D show several states of the switches 280 and 300 resulting in different modes of the controller switching unit 260 of the system of FIG. 8. These states of the switches 280 and 300 are controlled by the controller 390. In FIG. 9A, current is injected into the first MX lead 180 and received by the fourth MX lead 240. While this current travels through the body part 110, a resultant voltage is measured between the second MX lead 200 and the third MX lead 220. This measurement is tetrapolar because current is forced to flow between two leads and the resultant voltage is measured between two other leads.

In FIG. 9B, current is injected into the second MX lead 200 and received by the third MX lead 220. The resultant voltage is measured between the first MX lead 180 and the fourth MX lead 240. This measurement is also tetrapolar.

In FIGS. 9A and 9B, the first switch 280 and the second switch 300 are both in tetrapolar states since, for each of the switches 280 and 300, two distinct MX leads are involved in the impedance measurement. When both switch states are tetrapolar, the controller switching unit 260 is said to be in a tetrapolar mode. Thus, FIGS. 9A and 9B correspond to tetrapolar modes.

In a tetrapolar mode, the current input lead 320 is electrically connected to exactly one of the first MX lead 180 and the second MX lead 200 and the first voltage lead 360 is electrically connected to the other one of the first MX lead 180 and the second MX lead 200; likewise, the current output lead 340 is electrically connected to exactly one of the third MX lead 220 and the fourth MX lead 240 and the second voltage lead 380 is connected to the other one of the third MX lead 220 and the fourth MX lead 240.

The two tetrapolar modes shown in FIGS. 9A and 9B do not exhaust all the tetrapolar modes. For example, when the first switch 280 state is the same as the state shown in FIG. 9A and the second switch 300 state is the same as the state shown in FIG. 9B, the controller switching unit 260 is also in a tetrapolar mode. Generally, the controller switching unit 260 is in a tetrapolar mode when $n_1$, $n_2$, $n_3$ and $n_4$ are distinct, where $n_1$ and $n_2$ are leads from among the N leads 120 used to inject current into and receive current from the body part 110, and $n_3$ and $n_4$ are leads used to measure the resultant voltage.

In FIG. 9C, current is injected into the first MX lead 180 and received by the fourth MX lead 240. While this current travels through the body part 110, a resultant voltage is measured between the first MX lead 180 and the fourth MX lead 240. The second and third MX leads 200 and 220 are electrically unconnected to any of the N body leads 120 during this measurement. This measurement is bipolar because the pair of electrodes used for measuring a voltage is also used for current flow.

In FIG. 9D, current is injected into the second MX lead 200 and received by the third MX lead 220. The resultant voltage is measured between the same two leads 200 and 220. The first and fourth MX leads 180 and 240 are electrically unconnected during this measurement. This measurement is also bipolar.

In FIGS. 9C and 9D, the first switch 280 and the second switch 300 are both in bipolar states since, for each of the switches 280 and 300, only one MX lead is involved in the impedance measurement. When both switch states are bipolar, the controller switching unit 260 is said to be in a bipolar mode. Thus, FIGS. 9C and 9D correspond to bipolar modes.

In a bipolar mode, the current input lead 320 and the first voltage lead 360 are electrically connected to each other and to exactly one of the first MX lead 180 and the second MX lead 200, and the current output lead 340 and the second voltage lead 380 are electrically connected to each other and to exactly one of the third MX lead 220 and the fourth MX lead 240.

The two modes shown in FIGS. 9C and 9D do not exhaust all bipolar modes. For example, when the first switch 280 state is the same as the state shown in FIG. 9C and the second switch 300 state is the same as the state shown in FIG. 9D, the controller switching unit 260 is also in a bipolar mode. More generally, the controller switching unit 260 is in a bipolar mode when $n_1=n_3$ or $n_4$, and $n_2=n_3$ or $n_4$, where $n_1$ and $n_2$ are leads from among the N leads 120 used to inject and receive current, and $n_3$ and $n_4$ are leads used to measure the resultant voltage.

In addition to the tetrapolar and bipolar modes shown in FIGS. 9A-9D, there are also hybrid modes. FIG. 10 shows a hybrid mode of the controller switching unit 260 of FIG. 8. Here, the first switch 280 is in a tetrapolar state and the second switch 300 is in a bipolar state. In a hybrid mode, $n_1 \neq n_3$ and $n_2=n_4$, or $n_1 \neq n_4$ and $n_2=n_3$, where again $n_1$ and $n_2$ are used for current flow and $n_3$ and $n_4$ are used for voltage measurement.

In FIG. 10, the lead $n_1$ is electrically connected to the first MX lead 180 or to the fourth MX lead 240 via the multiplexer 160. The lead $n_2$ is connected to whichever of first MX lead 180 and the fourth MX lead 240 is not connected to the lead $n_1$. The lead $n_3$ is connected to the second MX lead 200 or the fourth MX lead 240, and the lead $n_4$ is connected to whichever of the second MX lead 200 and the fourth MX lead 240 is not connected to the $n_3$ lead. The third MX lead 220 is electrically unconnected during this hybrid measurement.

Figure 11:
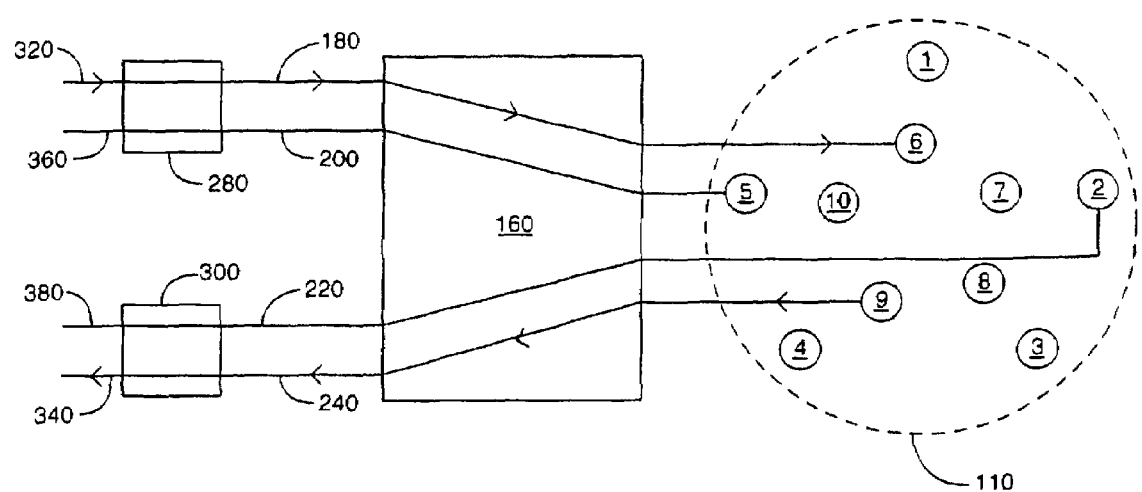
FIG. 11 shows electrical connections in a particular tetrapolar impedance measurement that employs the system of FIG. 8.

FIG. 11 shows electrical connections in a particular tetrapolar impedance measurement that employs the system 1000 of FIG. 8. For simplicity, the system 1000 has only N=10 leads, and the controller 390, the impedance module 400 and the diagnosis module 420 are not shown. In a different embodiment, N=32. Also not shown in the FIG. 11 is the second set of leads 440. The ten electrodes of the ten leads are shown: the first set of N/2=five electrodes 1-5 lie on the outside perimeter and the other set of five electrodes 6-10 lie on the inner perimeter.

All the electrodes 1-5 of the first set can be electrically connected to the first and fourth MX leads 180 and 240, and all the electrodes 6-10 of the second set can be connected to the second and third MX leads 200 and 220 via the multiplexer 160. In the example of FIG. 11, the connections shown are for one tetrapolar measurement in which $n_1=6$, $n_2=9$, $n_3=2$ and $n_4=5$, where electrode 6 is used to inject current into the body part 110 and electrode 9 is used to receive the current. The electrodes 2 and 5 are used to measure the resultant voltage. Although all electrodes of the ten leads are shown in FIG. 11, only the four wires of the electrically active leads appear.

In particular, current is generated by the impedance module 400 and sent to the current input lead 320. From there, the current travels to the first MX lead 180 via the first switch 280 and from there to the electrode 6 via the multiplexer 160. The current next travels through the body part 110 to the electrode 9 and then through the multiplexer 160 to the fourth MX lead 240. The current then flows to the current output lead 340 via the second switch 300 and then back to the impedance module 400. The resultant voltage is measured between the first and second voltage leads 360 and 380, which corresponds to the voltage between the electrodes 2 and 5. The first voltage lead 360 is connected to the electrode 2 via the first switch 280 and the multiplexer 160, and the second voltage lead 380 is electrically connected to the electrode 5 via the second switch 300 and the multiplexer 160. The controller 390 controls the states of the switches 280 and 300 and the multiplexing states in the multiplexer 160 that determine through which leads current flows and which leads are used to measure voltage.

Figure 12A:
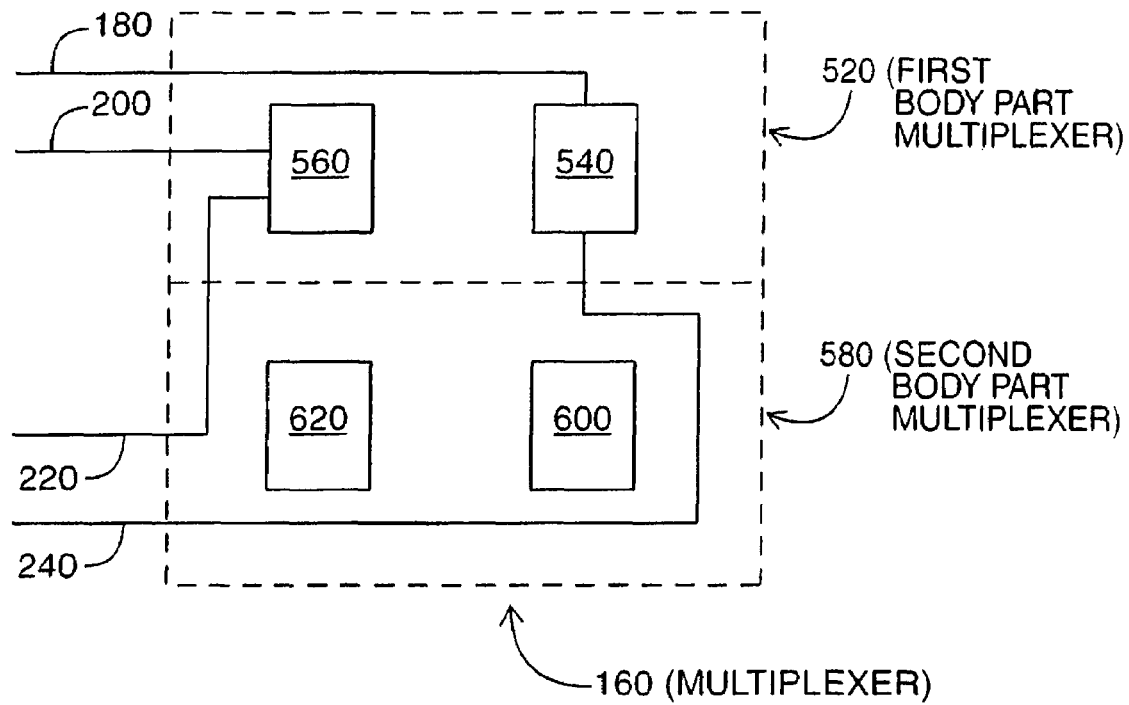
FIGS. 12A and 12B show the multiplexer of FIG. 8.

FIG. 12A shows the multiplexer 160 of FIG. 8 in an embodiment in which a body part is being compared to a homologous body part. The multiplexer 160 includes a first body part multiplexer 520 that includes a first body part A multiplexer unit 540 and a first body part B multiplexer unit 560. The multiplexer 160 also includes a second body part multiplexer 580 that includes a second body part A multiplexer unit 600 and a second body part B multiplexer unit 620. The first body part A multiplexer unit 540 is connected to the first MX lead 180 and the fourth MX lead 240. The first body part B multiplexer unit 560 is connected to the second MX lead 200 and the third MX lead 220. Although not shown in the interest of clarity, the second body part A multiplexer unit 600 is also connected to the first MX lead 180 and the fourth MX lead 240, and the second body part B multiplexer unit 620 is also connected to the second MX lead 200 and the third MX lead 220.

The first body part multiplexer 520 is used for multiplexing electrical signals to the first body part of the homologous pair. In particular, the first body part A multiplexer unit 540 and B multiplexer unit 560 are both capable of multiplexing current and voltage signals to and from the N leads 120. Likewise, the second body part multiplexer 580 is used for multiplexing electrical signals to the homologous body part. In particular, the second body part A multiplexer unit 600 and B multiplexer unit 620 are both capable of multiplexing current and voltage signals to and from the N leads 120, as described below.

Figure 12B:
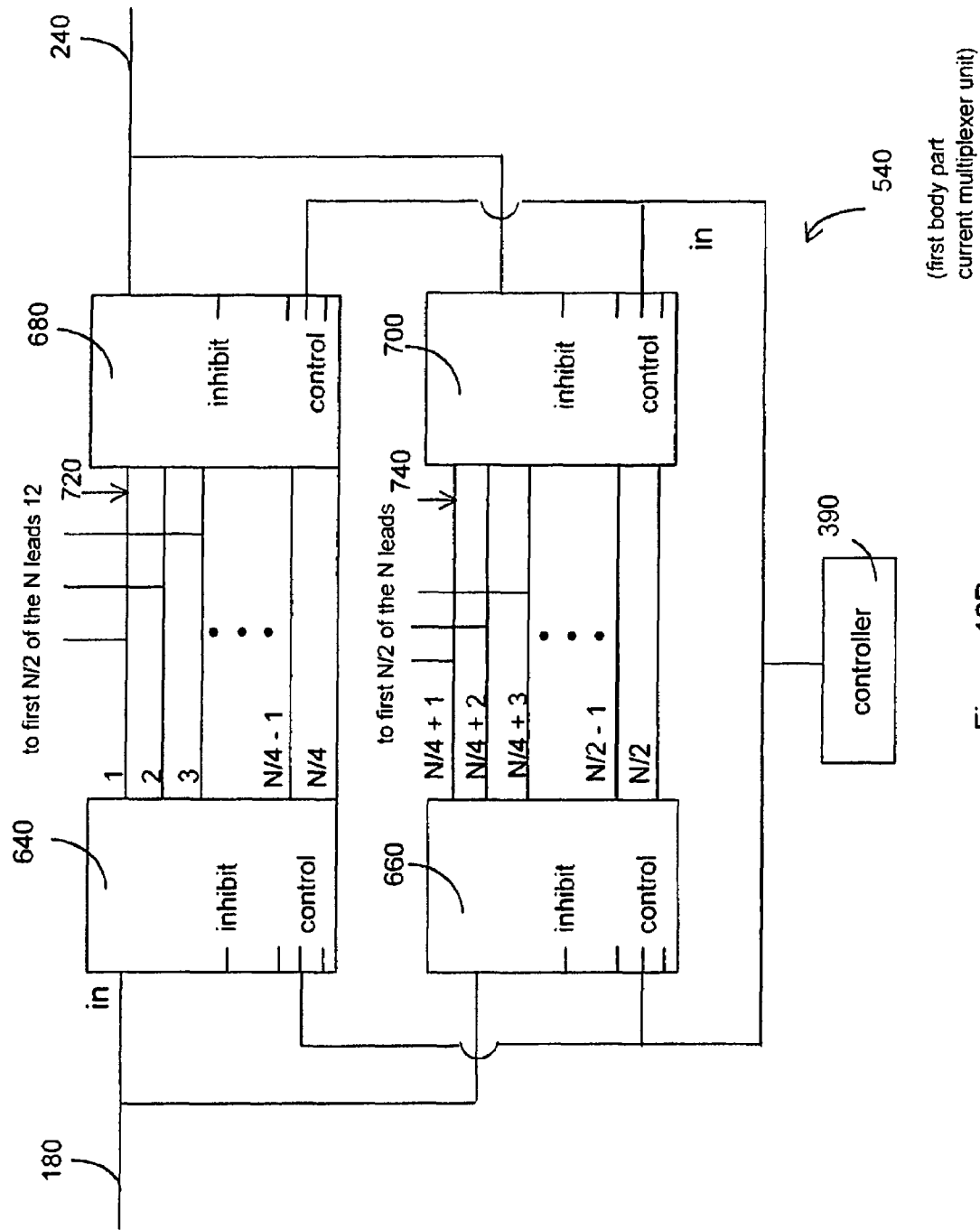

FIG. 12B shows the first body part A multiplexer unit 540 of FIG. 12A. The multiplexer unit 540 includes four one-to-N/4 multiplexers 640, 660, 680 and 700. These, for example, can be model number MAX4051ACPE manufactured by MAXIM™. The N/4 multiplexer current leads 720 connect the multiplexer 640 to the multiplexer 680, and N/4 multiplexer current leads 740 connect the multiplexers 660 and 700. In turn, the leads 720 and 740 are connected to the first N/2 of the N leads 120. The multiplexers 640, 660, 680 and 700 each have a configurable one bit "inhibit state" and $\log_2$ (N/4) bit "control state." The inhibit state can be either off (0) or on (1) and determines whether current can flow through the respective multiplexer 640, 660, 680 or 700. The control state determines through which one of the leads 720, 740 current flows. If N=32, then four bits are required for each active multiplexer (by "active" is meant that the inhibit state is off) and to specify a state, one for the inhibit state and three for the control state. For example, if the inhibit state of the multiplexer 640 is 1 (on) and the state of the multiplexer 660 is (0, 1, 0, 0), where the first bit is for the inhibit state, then current destined for the breast is directed to the tenth lead, provided the states of the switches 280 and 300 connect the current input lead 320 to the first MX lead 180, as previously described. If the states of the switches 280 and 300 do not connect the current input lead 320 to the first MX lead 180, but do connect the first voltage lead 360 to the first MX lead 180, then this lead 180, when the multiplexer 660 is in the state (0, 1, 0, 0), measures the resultant voltage with the tenth lead.

A similar binary code for the multiplexers 680 and 700 dictates through which one of the first 16 electrodes of the 32 leads 120 current is received from the breast, provided the states of the switches 280 and 300 connect the current output lead 340 to the fourth MX lead 240. If the fourth MX lead 240 is not connected to the current output lead 340, but is connected to the second voltage lead 220, then the fourth MX lead 240 is used for measuring the resultant voltage, provided the inhibit state of the multiplexer 680 or the multiplexer 700 is off.

The B multiplexer unit 560 is similar to the A multiplexer unit 540 in that it has four one-to-N/4 multiplexers analogous to 640, 660, 680 and 700. However, the one-to-N/4 multiplexers are capable of connecting with the second and third MX leads 200 and 220, instead of the first and fourth MX leads 180 and 240. Here, the inhibit and control states determine which electrode from among the other N/2 electrodes is used to deliver current or measure voltage.

Thus, by setting inhibit and control states, in coordination with the states of the switches 280 and 300, it is possible to direct current between any pair of the N leads 120 and to make a measurement of the resultant voltage between any pair of the N leads 120.

The inhibit and control states are set by the controller 390 with a shift-register and/or a computer. A direct digital stream can be sent to the shift register for this purpose.

The function of the second body part multiplexer 580 is analogous to that of the first body part multiplexer 520 and therefore need not be described further.

Figure 13:
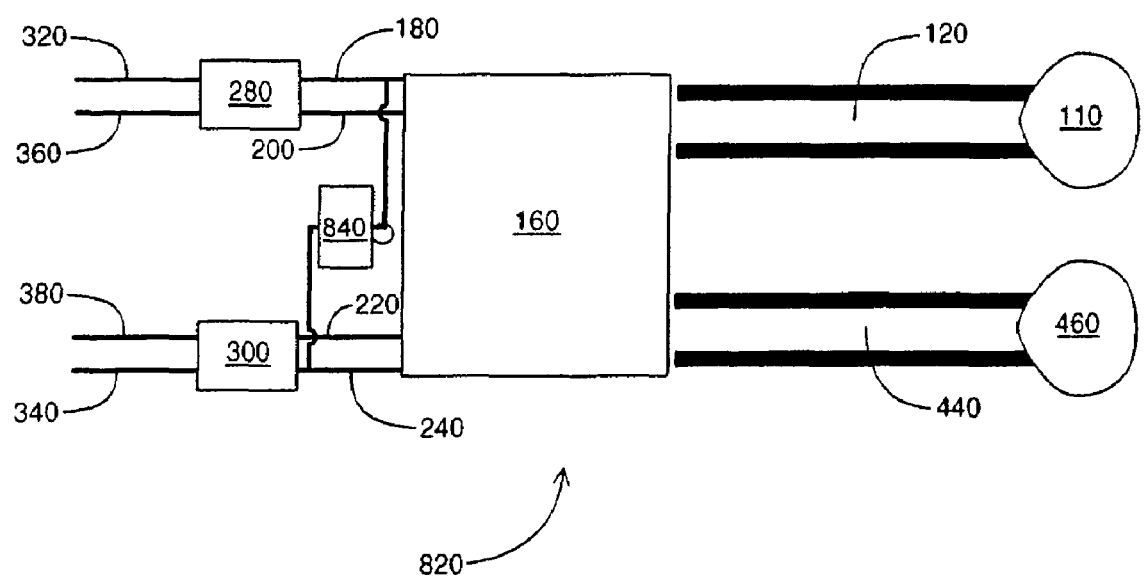
FIG. 13 shows a diagnostic system that includes an internal load in addition to the components of FIG. 8.

FIG. 13 shows a diagnostic system 820 that includes an internal load 840 in addition to the components described above in relation to FIG. 8. The internal load 840 is electrically connected to the first MX lead 180, the second MX lead 200, the third MX lead 220 and the fourth MX lead 240. The internal load 840 is used for at least one of internal testing of the system 820 and varying the measurement range of the system 820.

Using the first switch 280 and the second switch 300, the internal load 840 can be connected to the impedance module 400 in a tetrapolar mode or in a bipolar mode. The internal load 840 has a known impedance and therefore can be used to test the diagnostic system 820.

Additionally, the internal load 840 can be used to change the measurement range of the system 820. By attaching this internal load 840 in parallel with any load, such as the body part 110, the system 820 is capable of measuring larger impedances than would otherwise be possible. If the resistance of the internal load 840 is $R_{int}$ and is in parallel, the measured resistance R is given by $$R=(1/R_{load}+1/R_{int})^{-1}$$

where $R_{load}$ is the resistance of the load. Consequently, the measured resistance is reduced from the value without the internal load, thereby increasing the measurement range of the system 840.

Figure 14:
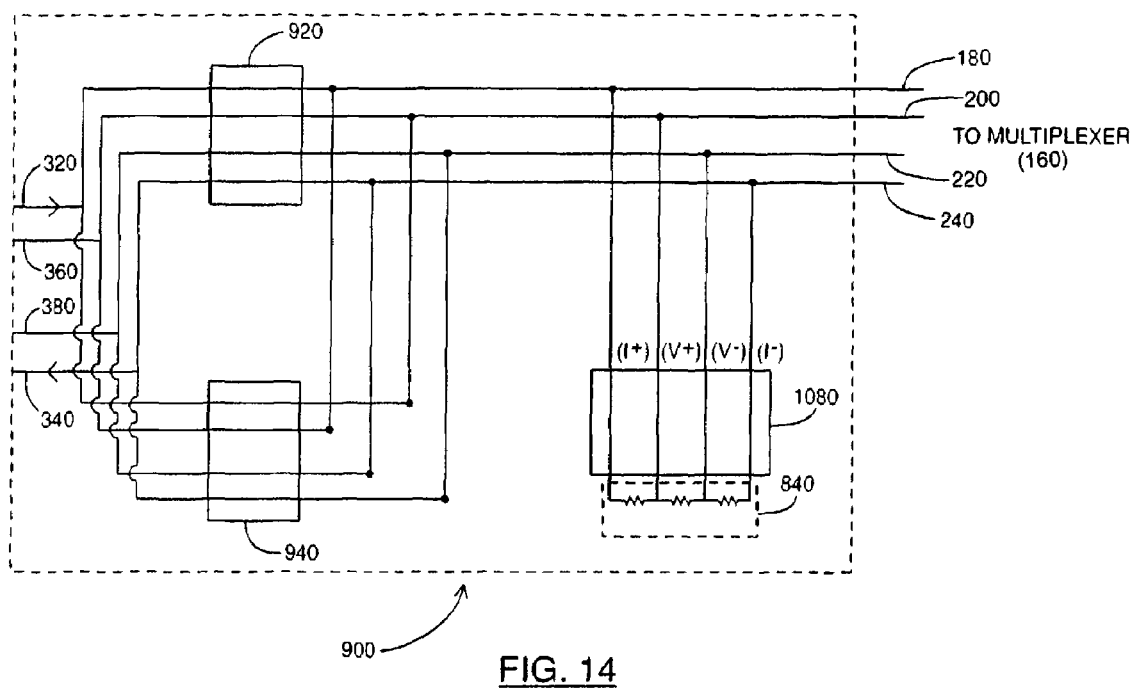
FIG. 14 shows one embodiment of the controller switching unit, according to the principles of the present invention.

The switches 280 and 300 allow current to flow between various pairs of electrodes on a body part, and resultant voltage to be measured between various pairs of electrodes, as described above with reference to FIGS. 8-13. In FIG. 14, another embodiment of the controller switching unit is shown that can be used to achieve the states of FIGS. 9A-D using a different electrical circuit topology. The controller switching unit 900 of FIG. 14 includes a first switch 920 and a second switch 940. The current input lead 320, the current output lead 340, the first voltage lead 360 and the second voltage lead 380 split to connect to both the first and second switches 920 and 940.

The switches 920 and 940 can be turned on or off and can be used to make tetrapolar and bipolar measurements. With only one of the switches 920 and 940 on, a tetrapolar measurement can be made. With both switches 920 and 940 on, a bipolar measurement can be made. For example, when the first switch 920 is on, and the second switch is off, the resultant functionality corresponds to that of FIG. 9A, albeit achieved with a different circuit topology. In this example, current flows from the impedance module 400 along the current input lead 320, through the first switch 920, and then to the first MX lead 180. From there, the current proceeds to the multiplexer 160. Current is received from the multiplexer 160 along the fourth MX lead, and delivered to the current output lead 340 via the first switch 920. The resultant voltage is measured between the second and third MX leads 200 and 220 with the use of the first and second voltage leads 360 and 380.

In another example, when the first switch 920 is off, and the second switch 940 is on, the resultant functionality corresponds to that of FIG. 9B. Here, current from the impedance module 400 travels along the current input lead 320, across the second switch 940, then jumps to the second MX lead 200. Current is received along the third MX lead 220, from where it jumps to the current output lead 340 via the second switch 940. The voltage is measured between the first and fourth MX leads 180 and 240 with the use of the first and second voltage leads 360 and 380.

In yet another example, the first and second switches 920 and 940 are both on, which corresponds to FIG. 9C or 9D. Precisely to which of these two figures this example corresponds is determined by the inhibit states of the multiplexer 160. For example, if the inhibit states of both of the one-to-N/4 multiplexers 640 and 660 are on, then bipolar measurements are performed with the second set of N/2 electrodes.

The controller switching unit 900 also includes an internal load switch 1080 that is connected to the internal load 840. The controller switching unit 900 and the internal load 840 are used to test the system and to increase the measurement range, as described above.

It should be understood that various modifications could be made to the embodiments described and illustrated herein, without departing from the present invention, the scope of which is defined in the appended claims. The present invention involves the use of an electrode array for measuring impedances of a breast to determine the condition thereof. However, although emphasis has been placed on describing a system for diagnosing breast cancer, the principles of the present invention can also be advantageously applied to other diseases of other body parts.

What is claimed is:

1. A system for diagnosing the possibility of disease in one of a first body part and a second substantially similar body part by impedance measurements, the system comprising:
   a first body part module for injecting a first current into the first body part and for receiving a corresponding first voltage signal;
   a second body part module for injecting a second current into the second body part and for receiving a corresponding second voltage signal;
   a correction module for obtaining a first correction factor for the first body part and a second correction factor for the second body part, the first and second correction factors accounting for impedances inherent in non-body part sources, the correction module including a magnitude correction module for calculating first and second magnitude correction factors, and a phase correction module for calculating first and second phase correction factors, where the first correction factor is composed of the first magnitude correction factor and the first phase correction factor, and where the second correction factor is composed of the second magnitude correction factor and the second phase correction factor; and
   an impedance module for calculating a first impedance from the first current, the first voltage signal and the first correction factor, and for calculating a second impedance from the second current, the second voltage signal and the second correction factor,
   wherein the first and second impedances are used to diagnose the possibility of disease.

2. The system of claim 1, wherein the non-body part sources that give rise to inherent impedances include skin covering the first and second body parts and system components.

3. The system of claim 1, wherein the correction module includes a magnitude correction table to calculate the first and second magnitude correction factors, the magnitude correction table containing calibration impedance magnitude ($|Z_{cal}|$) data and associated magnitude correction factor ($C_{mag}(|Z_{cal}|)$) data.

4. The system of claim 3, further comprising a calibration apparatus to form the magnitude correction table.

5. The system of claim 4, wherein the calibration apparatus includes an electrical model of the first body part, a variable interface resistance and the impedance module.

6. The system of claim 5, wherein the impedance module includes a bipolar unit for calculating a bipolar impedance, $Z_{BP}$, from a bipolar voltage measurement made by the first body part module on the first body part, a magnitude of the bipolar impedance used by the correction module to obtain the first correction factor.

7. The system of claim 6, wherein the correction module uses the magnitude correction table and the magnitude of the bipolar impedance to obtain the first magnitude correction factor, which is given by $C_{mag}(|Z_{BP}|)$.

8. The system of claim 7, wherein an uncorrected first impedance, $Z^{raw}$, is calculated by the impedance module from the first current and the first voltage signal.

9. The system of claim 8, wherein a magnitude of the first impedance, Z, is calculated by the impedance module according to $$|Z|=C_{mag}(|Z_{BP}|)\times|Z^{raw}|.$$

10. The system of claim 1, wherein the correction module includes a phase correction table to calculate the first and second phase correction factors, the phase correction table containing calibration impedance magnitude ($|Z_{cal}|$) data and associated phase correction factor ($C_{ph}(|Z_{cal}|)$) data.

11. The system of claim 10, further comprising a calibration apparatus to form the phase correction table.

12. The system of claim 11, wherein the calibration apparatus includes an electrical model of the first body part, a variable interface resistance and the impedance module.

13. The system of claim 12, wherein the impedance module includes a bipolar unit for calculating a bipolar impedance, $Z_{BP}$, from a bipolar voltage measurement made by the first body part module on the first body part, a magnitude of the bipolar impedance used by the correction module to obtain the first correction factor.

14. The system of claim 13, wherein the correction module uses information from the phase correction table and the magnitude of the bipolar impedance to obtain the first phase correction factor $C_{ph}(|Z_{BP}|)$.

15. The system of claim 14, wherein an uncorrected first impedance, $Z^{unc}$, is calculated by the impedance module from the first current and the first voltage signal.

16. The system of claim 15, wherein a phase of the first impedance, Z, is calculated by the impedance module according to $$\arg(Z)=C_{arg}(Z_{BP})\times\arg(Z^{unc}).$$

17. A method for diagnosing the possibility of disease in one of a first body part and a second substantially similar body part by impedance measurements, the method comprising:
    injecting a first current into the first body part;
    receiving a corresponding first voltage signal;
    injecting a second current into the second body part;
    receiving a corresponding second voltage signal;
    obtaining a first correction factor for the first body part and a second correction factor for the second body part, the first and second correction factors accounting for impedances inherent in non-body part sources, the step of obtaining including calculating first and second magnitude correction factors, and calculating first and second phase correction factors, where the first correction factor is composed of the first magnitude correction factor and the first phase correction factor, and where the second correction factor is composed of the second magnitude correction factor and the second phase correction factor;
    calculating a first impedance from the first current, the first voltage signal and the first correction factor with an impedance module; and
    calculating a second impedance from the second current, the second voltage signal and the second correction factor with the impedance module,
    wherein the first and second impedances are used to diagnose the possibility of disease.

18. The method of claim 17, wherein the non-body part sources that give rise to inherent impedances include skin covering the first and second body parts and system components.

19. The method of claim 18, wherein the step of calculating first and second magnitude correction factors includes using a magnitude correction table, the magnitude correction table containing calibration impedance magnitude ($|Z_{cal}|$) data and associated magnitude correction factor ($C_{mag}(|Z_{cal}|)$) data.

20. The method of claim 19, further comprising forming the magnitude correction table with a calibration apparatus that includes an electrical model of the first body part, a variable interface resistance and the impedance module.

21. The method of claim 20, further comprising:
    performing a bipolar voltage measurement on the first body part; and
    calculating a bipolar impedance, $Z_{BP}$, from the bipolar voltage, the magnitude of the bipolar impedance used to obtain the first correction factor.

22. The method of claim 21, wherein the magnitude correction table and a magnitude of the bipolar impedance are used to obtain the first magnitude correction factor, which is given by $C_{mag}(|Z_{BP}|)$.

23. The method of claim 22, further comprising calculating an uncorrected first impedance, $Z^{raw}$, from the first current and the first voltage signal.

24. The method of claim 23, wherein a magnitude of the first impedance, Z, is given by $$|Z|=C_{mag}(|Z_{BP}|)\times|Z^{raw}|.$$

25. The method of claim 17, wherein the step of calculating the first and second phase correction factors includes using a phase correction table to calculate the first and second phase correction factors, the phase correction table containing calibration impedance magnitude ($|Z_{cal}|$) data and associated phase correction factor ($C_{ph}(|Z_{cal}|)$) data.

26. The method of claim 25, further comprising forming the phase correction table with a calibration apparatus that includes an electrical model of the first body part, a variable interface resistance and the impedance module.

27. The method of claim 26, further comprising:
    performing a bipolar voltage measurement on the first body part; and
    calculating a bipolar impedance, $Z_{BP}$, from the bipolar voltage, a magnitude of the bipolar impedance used to obtain the first correction factor.

28. The method of claim 27, wherein the phase correction table and the magnitude of the bipolar impedance are used to obtain the first phase correction factor, which is given by $C_{ph}(|Z_{BP}|)$.

29. The method of claim 28, further comprising calculating an uncorrected first impedance, $Z^{raw}$, from the first current and the first voltage signal.

30. The method of claim 29, wherein a phase of the first impedance, Z, is given by $$\arg(Z)=C_{arg}(Z_{BP})\times\arg(Z^{unc}).$$

* * * * *